United States Patent [19]

Harris et al.

[11] Patent Number: 5,106,610

[45] Date of Patent: Apr. 21, 1992

[54] METHOD FOR DETERMINING THE DIURETIC POTENCY OF CANDIDATE DRUGS AS INHIBITORS OF THE ANTIDIURETIC HORMONE-ELICITED WATER CHANNEL

[75] Inventors: H. William Harris, Dover; Mark L. Zeidel, Wellesley, both of Mass.

[73] Assignee: Childrens Medical Center Corporation, Boston, Mass.

[21] Appl. No.: 458,591

[22] Filed: Dec. 29, 1989

[51] Int. Cl.$^5$ .................. G01N 33/15; G01N 24/00
[52] U.S. Cl. ........................ 424/7.1; 424/9; 514/836; 514/869
[58] Field of Search .............. 424/7.1, 9; 514/836, 514/869

[56] References Cited

PUBLICATIONS

Harris, H. W. et al., *Am. J. Physiol.*, 251(Cell Physiol 20): C274–C284 (1986).
Gutknecht, J., *Proc. Natl. Acad. Sci. USA*, 84: 6443–6446 (1987).
Parisi, M. et al., *Biochimica et Biophysica Acta*, 556: 509–523 (1979).
Harris, H. W. et al., *J. Membrane Biol.*, 96: 175–186 (1987).
Harris, H. W. et al., *Am. J. of Physiol.*, 258: F237–F243 (1990).
Harris, H. W. et al., *Am. J. Physiol.*, 259: F366–F370 (1990).
Shi, L. and Verkman, A. S., *Biophysical J.*, 55: 159A (1989).
Hoch, B. S. et al., *Am. J. Physiol.*, 256: F948–F953 (1989).
Shi, L et al., *Kidney Inter.*, 37: 400A (1990).
Zeidel, M. L. et al., *Kidney Inter.*, 37: 407A (1990).
Verkman, A. S. et al., *Nature*, 333: 268–269 (1988).
Strange, K. and Spring, K. R., *J. Membrane Biol.*, 96: 27–43 (1989).

*Primary Examiner*—Glennon H. Hollrah
*Assistant Examiner*—Gary E. Hollinden
*Attorney, Agent, or Firm*—Hamilton, Brook, Smith & Reynolds

[57] ABSTRACT

A method for determining the diuretic potency of candidate drugs as inhibitors of ADH-elicited water channels is disclosed. In a preferred embodiment, such diuretic potency of candidate drugs is determined by suspending vesicles containing ADH water channels in an aqueous suspending medium, incorporating the candidate into the suspension, rapidly changing the pH of the suspending medium and thereafter detecting the proton permeability of the water channels. The proton permeability in the presence of the candidate drug can then be compared to the proton permeability of water channels under similar conditions without the presence of the candidate drug to determine the diuretic potency of the candidate drug to inhibit ADH-elicited water channels.

6 Claims, 3 Drawing Sheets

METHOD FOR DETERMINING THE DIURETIC POTENCY OF CANDIDATE DRUGS AS INHIBITORS OF THE ANTIDIURETIC HORMONE-ELICITED WATER CHANNEL

GOVERNMENT SUPPORT

Research leading to this invention supported by the National Institutes of Health and the American Heart Association.

BACKGROUND OF THE INVENTION

Aqueous fluids account for approximately half oa normal adult's body weight. These fluids contain osmotically active solutes. The proper concentrations of solutes within bodily fluids are maintained within narrow limits despite large variations of both solute and water intake by changes in the volume of water excreted per day. Thus, proper renal processing of aqueous fluids, including modulation of water excretion, is critically important to the maintenance of good health.

Renal processing of the body's solutes and water content first involves filtering of blood at lomeruli to separate retained blood cells and proteins from filtered solutes and water. The majority of the filtered solutes and water are returned to the body's circulation via selective absorption by renal tubules. In the proximal portion of renal tubules, water reabsorption occurs as a result of active reabsorption f solutes. In contrast, in distal portions of the tubules, solute and water reabsorption occur by separate processes. When an excess of body water is present, there is reabsorption of body solutes and excess water flows through the distal nephron to the bladder as dilute urine. In periods of dehydration, water is osmotically reabsorbed such that a concentrated hypertnic urine is formed. Osmotic reabsorption of water in the distal nephron segment, called the collecting duct, is modulated by antidiuretic hormone (ADH). Changes in collecting duct water permeability are accomplished through control of the water permeability of the apical membranes of epithelial cells that line this segment. ADH causes the insertion of water channels into epithelial cell apical membranes. These water channels were originally contained in vesicles within the cytoplasm of these epithelial cells. ADH causes water channel insertion by fusion of the water channel-containing vesicles with the apical membrane. Removal of the ADH stimuli causes removal of water channels from the apical membrane by retrieval of the water channel-containing membrane into the epithelial cell cytoplasm.

A variety of diseases are associated with retention of excess body water. These include, for example, liver failure, heart disease and syndrome of inappropriate ADH secretion (SIADH). These diseases are difficult to manage therapeutically because of the kidney's dissociation of solute and water reabsorption, as discussed above.

One of the major problems preventing effective removal of excess body water in these diseases in the lack of ability to selectively block renal water reabsorption. Presently, these diseases are treated with a variety of diuretic agents. However, currently available diuretics block renal tubular water reabsorption by inhibiting tubular solute reabsorption. Thus, in order to remove excess body water, there is an obligatory loss of large amounts of body solutes that results in the depletion of body ionic stores, especially sodium, potassium and chloride ions.

It is apparent, therefore, that there has been a long-standing need for better and more selective diuretics. Despite the need, it has been extremely difficult, or impossible, to screen compounds for their diuretic potency and selectivity in blocking water flow across ADH water channels. This is largely due to the fact that water flow through the water channels and lipid bilayers is so rapid that it nearly precludes any practical way of measuring such flow.

SUMMARY OF THE INVENTION

This invention relates to Applicants' discovery that ADH water channels is vesicles derived from renal apical membranes ar permeable to protons. As a result, the diuretic potency of a candidate drug to inhibit ADH-elicited water channels can be assessed by determining the effect that the candidate drug has on the proton permeability of ADH water channels.

In one embodiment, the diuretic potency of a candidate drug to inhibit ADH-elected water channel is determined by forming a suspension of vesicles containing ADH water channels in an aqueous suspending medium. The candidate drug is incorporated into the suspension in an amount which could produce a significant change in the water permeability of the ADH water channel if the candidate drug possesses water-inhibitory properties. The pH of the suspending of the water channels is detected. The proton permeability of the water channels in the presence of the candidate drug is compared to the proton permeability of water channels under similar conditions but without the presence of the candidate drug to determine the diuretic potency of the candidate drug to inhibit ADH-elicited water channels.

In another embodiment, the invention provides a method for therapeutically treating a patient having a disease associated with excess body water. This method comprises amount of a diuretic drug capable of inhibiting ADH-elected water channels.

This invention provides convenient and practical methodology for the screening of a large number of candidate drugs to determine their diuretic potency for inhibiting ADH-elicited water channels. Thus, the invention provides a practical way to screen candidate drugs that inhibit ADH water channels while not interfering with renal reabsorption of other solute ions, such as sodium, potassium and chloride. It also provides the ability to study and quantitate the properties the ability to study and quantitate the properties of ADH water channels. It further provides a technique for identifying ADH water channels which should prove useful in their purification. Finally, the invention provides a therapeutic treatment for patients suffering from a disease associated with excess body water.

DETAILED DESCRIPTION OF THE INVENTION

Figure 1:
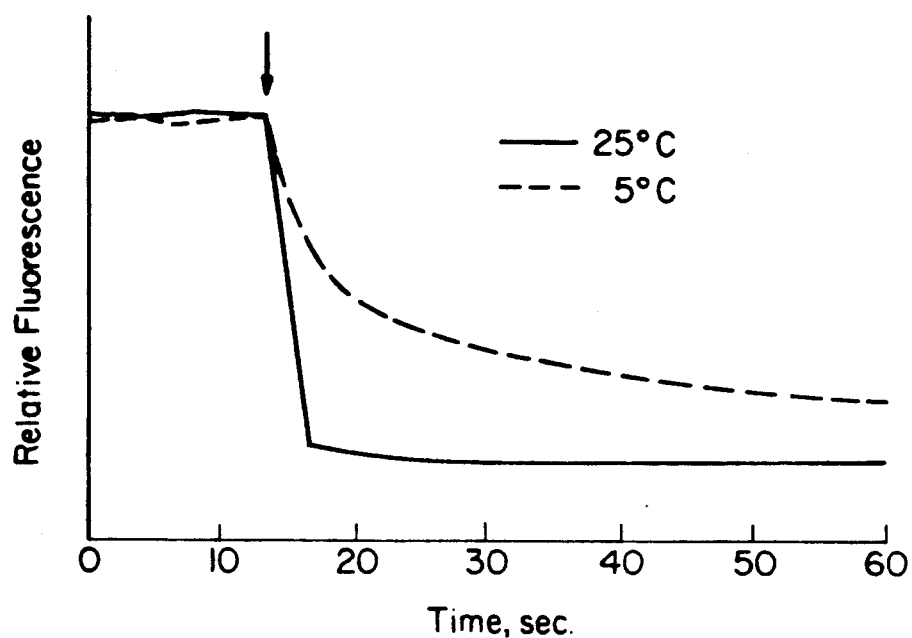
FIG. 1 is a plot of relative fluorescence versus time illustrating the effect of two temperatures on oP change in F-dextran loaded vesicles containing ADH water channels.

As used herein, the term "diuretic potency of a drug to inhibit ADH-elicited water channels" means to ability of a compound or substance to inhibit significantly the flow of water through the aqueous pores that constitute the ADH water channels of renal apical membranes. Such inhibition could occur through a number of mechanisms, including direct blockade of the channels as well as modification of proteins or lipids that in turn change the structure of the channels to decrease their permeability to wear.

Endocytic vesicles containing ADH water channels can be obtained from a variety of sources. These include, for example, the homogenized papillas of kidneys from Bratteboro rats, New Zealand white rabbits and domestic cattle. A convenient source for ADH water channel-containing vesicles is the intercellular vesicles derived from the apical membranes of ADH-stimulated toad urinary bladders. The membranes of these retrieved vesicles are derived from vesicles that store high concentrations of ADH water channels. These vesicles, called aggrephores, are large storage vesicles located immediate beneath the partial membrane. Techniques for obtaining a partially purified vesicle fraction containing such vesicles have been published. See Harris, H. W. et.al., *J. Memb. Biol* 96:175-186 (1987), the teachings of which are incorporated by reference.

Suitable vesicles could also be prepared by other techniques. For example, ADH water channel components could be incorporated into artificial liposomes containing an entrapped flurorphore.

The ADH water channel-containing vesicles are suspended in an aqueous medium sufficient to allow dissociation of protons ($H^+$) and anins, such as hydroxyl ($PH^-$) ions, from their parent compounds. A wide variety of aqueous solutions, including pure water, can be used in this assay.

Candidate drugs can be tested by the assay of this invention to determine their diuretic potency to inhibit ADH-elected water channels. These candidate drugs can be small molecules, peptides, proteins, etc. The candidate drugs must be sufficiently soluble, however, in an aqueous medium to allow a sufficient amount to dissolve so that their inhibiting potential can be determined. Incubation conditions and duration will depend on the nature of individual compounds tested.

For assay, the vesicles containing ADH-elicited water channels are suspended in an aqueous medium, preferably one that is stirred continuously. Proton flux through the ADH water channels in these vesicles is created by establishing a significant proton concentration differential between the suspending medium and intravesicular medium. This concentration differential establishes a driving force to create portion flux through the water channels if the water channels remain proton permeable. The proton concentration differential can be created conveniently by rapidly changing the pH of the aqueous suspending medium compared to the intravesicular medium. For example, acid can be added directly to the suspending medium to lower the pH thereby providing a suspending medium having a significantly higher concentration of protons that the intravesicular medium. Alternatively, an aliquot of alkali, such as sodium hydroxide, could be added to the suspending medium to raise the pH thereby decreasing the proton concentration of the suspending medium compared to the intravesicular proton concentration. Alternatively, the proton concentration of the extravesicular medium could be altered by initiation of a chemical reaction that produces or consumes protons.

Because proton flux is rapid, it si preferred to detect a change in intravesicular proton concentration by rapid detection means, such as optical, nuclear magnetic resonance (NMR) or certain dyes. The experimental work described herein was conducted using a pH-sensitive flurorphore, fluorescin, which was bonded to dextran to assist in retaining the flurorphore within the water channel-containing vesicles. This technique has been described in the literature. See for example, Harris, H. W., Wade, J. B. and Handler, J. S., "Fluorescent Markers to Study Membrane Retrieval in Antidiuretic Homo-Treated Toad Urinary Bladder", published in *Am J. Physiol.* 251:C274-C284 (1986), the teachings of which are incorporated by reference. Fluoroescein is a preferred pH-sensitive flurorphore because its intravesicular fluorescence correlates linearly with pH over the pH range of 6.0 to 8.0, permitting accurate estimation of intravesicular pH.

In order to slow the rate at which intravesicular pH changes, a buffer is employed. The buffer is loaded into the vesicles in a manner similar to the loading of the pH-sensitive flurorphore or other pH indicator. Suitable buffers have a group with a dissociation constant (pKa) within the physiological pH range. Examples of suitable buffers include HEPES, TRis and solium phosphate buffers.

Since proton permeability has been found to be closely related to water permeability of ADH water channels, the detection of proton permeability serves as a convenient measure of water permeability. The diuretic potency of a particular candidate drug to inhibit ADH-elicited water channels is assessed by paired experiments in which one aliquot of vesicles is treated with the candidate drug and the other aliquot serves as its untrated paired control. The rate of proton equilibration across these two groups of vesicles is compared after each is subjected to an identical pH gradient. The rate of proton equilibration is recorded and the data analyzed to derive an equation that described these rates. The rates of these two groups of vesicles are then compared to determine if the candidate diuretic compound inhibits proton flow across the membranes of these vesicles. If it does, it will also inhibit water permeability.

It is desirable, of course, that diuretic drugs possess additional properties beyond their ability to inhibit the proton and water permeabilities of ADH water channels. Particularly preferred diuretic drugs will have a selective effect in inhibiting ADH-elected water channels. That is, such selective diuretic drugs will inhibit ADH-elicited water channels without significantly effecting other renal reabsorption processes, such as reabsorption of solutes such as sodium, potassium and chloride ions. Candidate drugs found to inhibit ADH-elicited water channels can be tested for their effects on other renal processes by employing perfused renal segments, and/or renal epithelial cells. Such techniques are well knows to those skilled in the art. See, for example, Hock, B., Gorfein, P. C., Linzer, D., Fusco, M. J. and Levine, S. C., "Mercurial Reagents Inhibit Flow Through ADH-Induced Water Channels in Toad Bladder", *Am. J. Physiol.* 256:F948-F953 (1989), the teachings of which are hereby incorporated by reference.

Diuretic drugs should also non-toxic, as defined by their lack of effects on other bodily transport systems, cell and organ machinery or higher physilogic functions. The presence or lack of such effects can be tested in live mammals, such as Brattleboro rats, by techniques knows to those skilled in the art.

Diuretic drugs found to inhibit the ADH-elicited water channels can be used to treat patients having a disease associated with excess body water. Such treatments will involve the administration to the patient of therapeutically effective amounts of the diuretic drug capable of inhibiting ADH-elected water channels. In most cases, it will be preferred to employ such a diuretic drug which is also selective in its inhibition of ADH-elicited water channels. Thus, the selective diuretic drug will inhibit ADH-elicited water channels without having an significant effect on other renal processes and which is non-toxic, as defined above.

Administration of such diuretic drugs can be by medically accepted techniques, including intravenous, eternal, etc. Appropriate amounts or dosages will vary from individual to individual and by disease, of course. Appropriate dosages can be calculated by those skilled in the art taking such factors into account.

Although the discussion above has emphasized methods for finding diuretics which inhibit ADH water channel permeability, anti-diuretics which increase ADH water channel permeability are also useful and can be found employing the assay techniques of this invention. Such anti-diuretics, which would increase ADH water channel permeability per molecule of ADH, could be used, for example, in treating dehydrated patients.

The invention is further illustrated by the following specific examples.

EXAMPLE 1

Proton Permeability at 5° and 25°

Endocytic vesicles from the bladder of Dominican toads were ADH stimulated and loaded with fluoroescein bound to dextran (F-dextran) following the procedures of Harris et.al., "Apical Membrane Vesicles of ADH-Stimulated Toad Bladder Are Highly Water Permeable,"*Am. J. Physiol.* In Press, (1989); Harris, H. W., et.al., "Fluorescent Markers to Study Membrane Retrieval in Antidiuretic Hormone-Treated Toad Urinary Bladder," *Am. J. Physiol.*, 251:C274-C284 (1986). Briefly, the procedures were as follows.

Dominican toads (*Bufo marinus*), obtained from National Reagents, Bridgeport, CT, were employed. Urinary bladders of *Bufo marinus* were prepared and mounted on cannulas as small sacs. After a 20 minute interval of ADH stimulation (50 mU/ml), the apical surfaces of bladders were exposed to solutions containing 50 mg/ml of F-dextran (Av. Mol. Wt. 70,000 Daltons) and 0-20 mg NaCl, 30 Mm KCl, and 1-20 mL HEPES, pH 8.0, for an interval of 5 minutes followed by termination of ADH stimulation and incubation for an additional 10 minutes. The solution containing the F-dextran was then removed, the bladders rinsed to remove all extracellular F-dextran. The intermediate pellet fraction obtained from centrifugation of the cell was used. F-dextran loaded vesicles were washed repeatedly to remove F-dextran and partially purified by differential centrifugation. In the absence of ADH, no detectable fluorescence was present in this vesicle fraction despite apical membrane exposure to F-dextran.

Standard cuvette fluorescence measurements were performed using an SLM-Aminco 500C spectrofluorimeter (excitation wavelength 499 nm). Stopped-flow measurements were performed in a High Tech stopped-flow device (50 msec dead time) connected to a Photon Technologies Alphascan Fluorimeter. One syringe contained a concentrated vesicle suspension and antifluoroscein antibody while the other contained buffer with sufficient HCl to change the final extravesicular pH as indicated. Data from 3-5 determination performed on a single day were averages. Results were fitted to single exponentials and $\tau$ was converted to permeability using the following equation:

$$J_{H+} = (P_{H+}) \times (\Delta C) \times (A)$$

where $J_{H+}$ is the flux rate of protons in mole/sec, $P_{H+}$ is the permeability coefficient of protons in cm/sec, $\Delta C$ is the concentration gradient for protons across the vesicle membrane at the start of the experiment in mole/cm$^3$, and A is the surface area of a single F-dextran containing vesicle ($7.1 \times 10^{-10}$ cm$^2$). See Harris, H. W., et.al., "Isolation and Characterization of Specialized Regions of Toad Urinary Bladder Apical Plasma Membrane Involved in the Water Permeability Response to Antidiuretic Hormone," *J. Memb. Biol.*, 96:175-186 (1987). $J_{h+}$ was calculated by multiplying $1/\tau$ by the amount of buffer (in moles) in an individual vesicle (single vesicle volume was $1.41 \times 10^{-14}$ cm$^3$). $\tau$ is the mathematical term representing the time for the process to be ⅔ completed. Estimates of vesicle volume and surface area were calculated from dimensions of vesicles loaded with horseradish peroxides (HRP) instead of F-dextran. Electron microscopic examinations of HRP-loaded vesicles showed that 89% were spherical in shape with a radius of $7.5 \times 10^{-6}$ cm and a volume/surface area ratio of $2.5 \times 10^{-6}$ cam.

The effect of changing extravesicular pH from 8.0 to 6.0 intravesicular fluorescence at 25° C. and 5° C. was determined. The extravesicular pH was lowered by abrupt addition of a small volume of 2N HCl. The results are plotted in FIG. 1. As can be seen from FIG. 1., $J_{H+}$ was markedly slowed by the temperature reduction from 25° C. to 5° C.

EXAMPLE 2

The effect of Buffer Concentration on Proton Permeability

Figure 2:
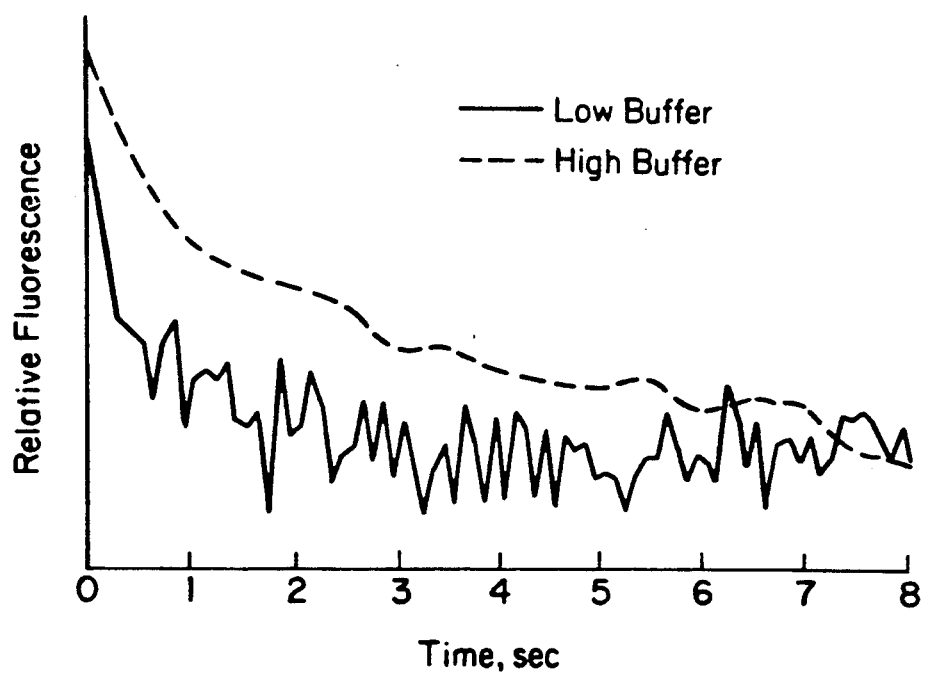
FIG. 2 is a plot of relative fluorescence versus time illustrating the effect of buffer concentration on the rate of pH change in F-dextran-loaded vesicles containing ADH water channels.

The procedures and materials of Example 1 were employed, except as where indicated differently. Vesicles were loaded, prepared and maintained in 20 mM ("high buffer") or 2 mM ("low buffer") HEPES buffer at pH 8.0. The temperature was maintained at 25°. The pH outside the vesicles was abruptly lowered to 6.0 and fluorescence was measured over time for the high and low buffer systems. The results are plotted in FIG. 2 which illustrates that the rate of decay of the imposed pH gradient varied with changes in the intravesicular buffer concentration. When the lumens of F-dextranladed vesicles were buffered with 20 mM HEPES, the time constant of the decline in $pH_i$ was given by a $\gamma$ of 7.2 sec. and yielded a $P_{H+}$ of $2.2 \times 10^{-3}$ cm/sc. The close agreement of $O_{H+}$ values under conditions of low and high intravesicular HEPES concentrations indicates that, in this range of added buffer, the added buffer itself and not other vesicle components dominates vesicle buffer capacity. The change in $\tau$ and the constancy of $P_{H+}$ as a function of intravesicular buffer concentration indicates that the fluorescence measurements reflected actual proton flux across the vesicle membrane.

EXAMPLE 3

Effect of pCMBS on Proton Permeability

Figure 3:
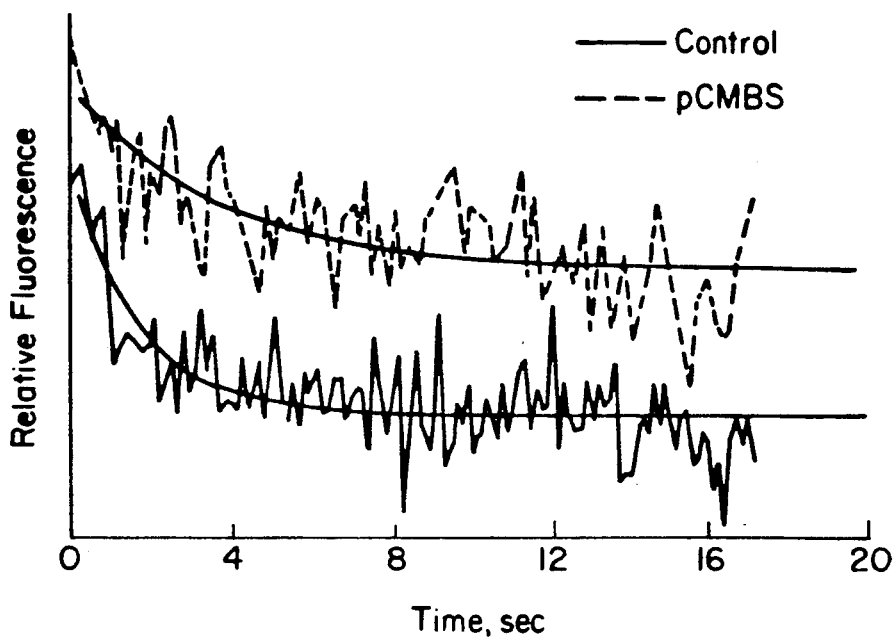
FIG. 3 is a plot of relative fluorescence versus time illustrating the effect of parachloromercuribenzene sulfonate (pCMBS) on the rate of pH change as detected by fluorescence in F-dextran loaded vesicles containing ADH water channels.

The effect of pCMBS on the rate of pH change in F-dextran loaded vesicles was determined. The materials and procedures of Example 1 were employed, except as noted. In vesicles containing 17.6 mM HEPES, pH 8.0, the extravesicular pH was abruptly lowered to 6.0 after one hour preincubation at 4° C. in the absence ("control") or presence ("pCMBS") of 1 of mM pCMBS. The results are plotted in FIG. 3. As illustrated, preincubation of vesicles with pCMBS inhibited 54% of $o_{H+}$ in F-dextran loaded vesicles. Control $p_{H+}$ was $3.9 \pm 0.5 \times 10^{-3}$ cm/sec (n−5; p<0.005 compared to control; unpaired t test).

The inhibitory effect of pCMBS was not shared by another sulfhydryl reagent, n-ethylmaleimide (NEM, 2 mM; vesicles were pretreated for 1 h with NEM in HEPES buffer on ice). Inpaired experiments, $p_{H+}$ was $5.6 \pm 0.2 \times 10^{-3}$ cm/sec in the absence and $6.2 \pm 0.9 \times 10^{-3}$ cm/sec (NS compared to control) after pretreatment with NEM. Unlike pCMBS, NEM pretreatment has no inhibitory effect on water flux across the toad bladder or human erythroycte membrane. See Ojcius, D. M. and Solomon, A. K., "Sites of p-chloromercuribenzendsulfonate inhibition of red cell urea and water transport", *Biochim. Biophys. Acta* 942:73–82 (1988). Phloretin inhibits both ADH-stimulated urea flux in toad bladder and $J_{H+}$ across artificial planar lipid bilayers. See Gutknecht, J., "Proton/ Hydroxide Conductance and Permeability through Phospholipid Bilayers," *Proc. Natl. Acad. Sci. USA*, 84:6443–6556 (1987); Levine, S. D., et.al., "Effect of Phloretin on Water and Solute Movement in the Toad Urinary Bladder," *J. Clin. Invest.*, 52:1435–1442 (1973). Phloretin was without effect, however, on apical membrane vesicle $J_{H+}$. In paired studies, control $P_{H+}$ was $2.4 \pm 4.0 \times 10^{-3}$ cm/sec; for phloretin-treated vesicles $P_{H+}$ was $2.6 \pm 0.4 \times 10^{-3}$ cm/sec. Vesicles were exposed to phloretin for 30 min. prior to assay; stopped flow studies were performed in the continued presence of phloretin.

EXAMPLE 4

The Effect of Inward and Outward Proton Fluxes

Figure 4:
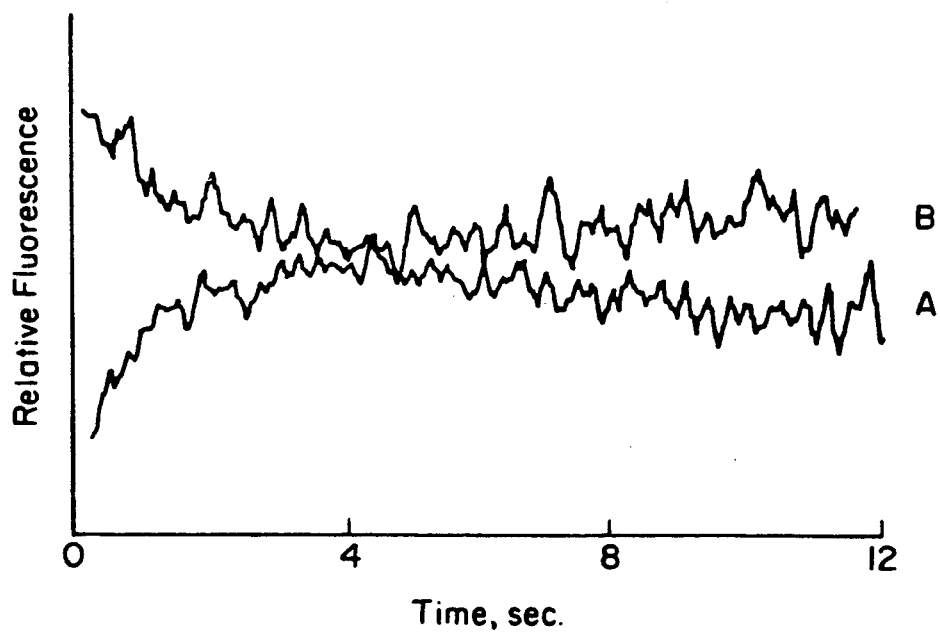
FIG. 4 is a plot of relative fluorescence versus time illustrating the symmetry of inward and outward proton fluxes in F-dextran loaded vesicle containing ADH water channels.

The effect of inward and outward proton fluxes was determined employing the procedures and materials of Example 1, except as noted. Vesicles were preincubated at pH 8.0 and diluted into pH 6.0 (tracing A), or preincubated at pH 6.0 and diluted to pH 8.0 (tracing B). The results are plotted in FIG. 4. As can be seen, the rate of proton flux was the same whether the luminal contents of the vesicles or the outside medium was more acidic at the outset of the experiment ($P_{H+}$ for pH 8.0 to 6.0, $3.9 \pm 0.5 \times 10^{-3}$ cm/sec; $p_{H+}$ for pH 6.0 to 8.0; $3.9 \pm 0.2 \times 10^{-3}$ cm/sec).

EXAMPLE 5

The effect of Baryng Temperature on Proton Flux

Figure 5:
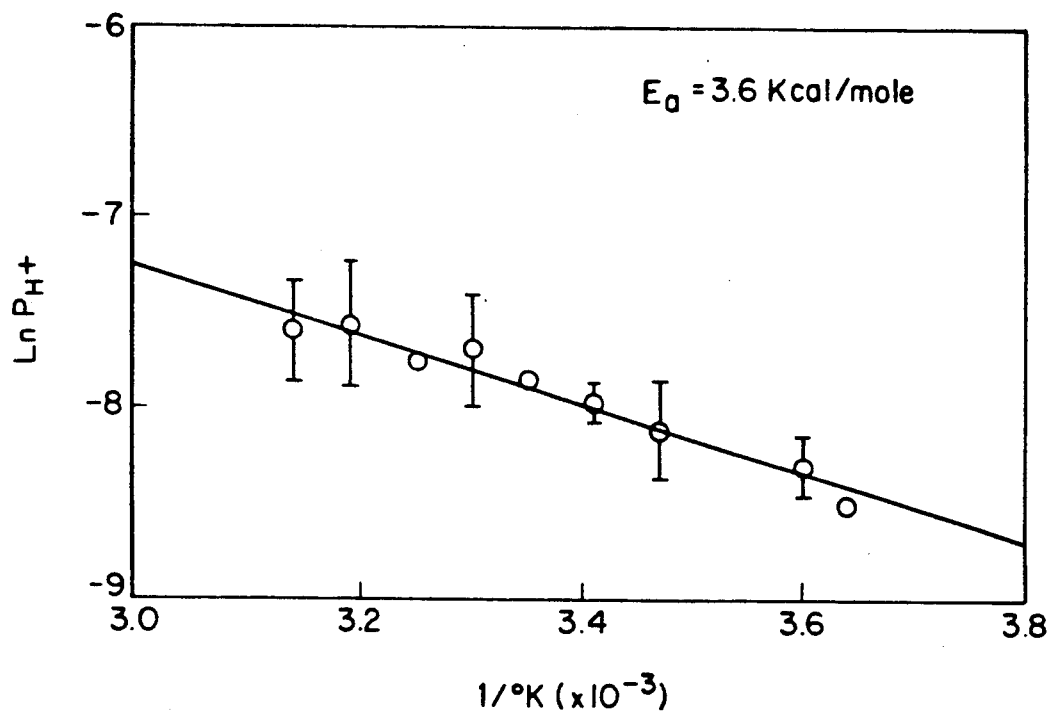
FIG. 5 is an Arrhenius plot illustrating the effect of varying temperature on vesicle proton permeability ($P_{H+}$).

The effect of barying temperature on proton flux was studied by constructing an Arrhenius plot for the proton permeation across membrane of toad bladded vesicles containing ADH water channels following the procedures and applying the materials of Example 1, except as noted. Measurements were taken at various temperatures, as indicated, and the results are plotted in FIG. 5. Each point represents mean $\pm$ SE of 3–4 different experiments; correlation coefficient for the fitted line was 0.979. The calculated activation energy of 3.6 kcal/mole indicates portion flux via channels containing water; values greater than 10 are obtained when protons diffuse across lipid bilayers, Butknecht, J., "Proton/Hydroxide Conductance and Permeability Through Phospholipid Bilayers," *Proc. Natl. Acad. Sci. USA*, 84:6443–6556 (1987); Kachadorian, W. A., et.al., "Temperature Dependence of ADH-Induced Water Flow and Intamembranous Particle Aggregates in Toad Bladder," *Science*, 205:910–914 (1979).

Equivalents

Those skilled in the art will recognize, or be able to ascertain using no more than routine experimentation, many equivalents to the specific embodiments described herein. Such equivalents are intended to be encompassed by the following claims.

What is claimed is:

1. A method for determining the diuretic potency of a candidate drug to inhibit ADH-elicited water channels comprising determining the effect the candidate drug has on the proton permeability of ADH water channels.

2. A method for determining the diuretic potency of a candidate drug to inhibit ADH-elicited water channels, comprising:
    (a) forming a suspension of vesicles containing ADH water channels in an aqueous suspending medium;
    (b) incorporating the candidate diuretic drug into the suspension of vesicles containing ADH water channels in an amount sufficient to produce a significant change in the water permeability of the ADH water channels if the candidate drug possesses inhibitory properties;
    (c) rapidly changing the pH of the aqueous suspending medium;
    (d) detecting the proton permeability of the water channels in response to the rapid pH change of the suspending medium; and
    (e) comparing the proton permeability of the water channels in the presence of the candidate drug to the proton permeability of water channels under similar conditions but without the presence of the candidate drug to determine the diuretic potency of the candidate drug to inhibit ADH water channels.

3. A method of claim 2 wherein the pH of the suspending medium is rapidly decreased by adding acid thereto.

4. A method of claim 3 wherein a pH-sensitive fluorophore is incorporated into the vesicles prior to rapidly changing the pH of the suspending medium and proton permeability of the water channels is determined by detecting fluorescence from said flurorphore after rapidly changing the pH of the suspending medium.

5. A method of claim 4 wherein the pH sensitive flurorphore comprises fluoroescein bound to dextran.

6. In a determination of ADH water channel permeability, the improvement comprising determining proton permeability of such channels.

* * * * *